US012796953B2

(12) United States Patent
Clark et al.

(10) Patent No.: US 12,796,953 B2
(45) **Date of Patent: *Nov. 17, 2026**

(54) CATHETER WITH COMBINED POSITION AND PRESSURE SENSING STRUCTURES

(71) Applicant: BIOSENSE WEBSTER (ISRAEL) LTD., Yokneam (IL)

(72) Inventors: Jeffrey L. Clark, Castaic, CA (US); Meir Bar-Tal, Haifa (IL); George Kamin, Arcadia, CA (US); Avram Dan Montag, Haifa (IL); Mark Stanley, Seal Beach, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/803,161

(22) Filed: Aug. 13, 2024

(65) Prior Publication Data

US 2024/0398254 A1 Dec. 5, 2024

Related U.S. Application Data

(63) Continuation of application No. 17/561,251, filed on Dec. 23, 2021, now Pat. No. 12,059,244, which is a (Continued)

(51) Int. Cl.
*A61B 5/00* (2006.01)
*A61B 5/06* (2006.01)
(Continued)

(52) U.S. Cl.
CPC .............. *A61B 5/062* (2013.01); *A61B 5/065* (2013.01); *A61B 5/6852* (2013.01); (Continued)

(58) Field of Classification Search
CPC ....... A61B 5/062; A61B 5/065; A61B 5/6852; A61B 5/6885; A61B 18/1492;
(Continued)

(56) References Cited

U.S. PATENT DOCUMENTS 5,391,199 A 2/1995 Ben-Haim
5,568,809 A 10/1996 Ben-Haim
(Continued)

FOREIGN PATENT DOCUMENTS

CN 1168625 A 12/1997
CN 101627901 A 1/2010
(Continued)

OTHER PUBLICATIONS

Australian First Office Action dated Jul. 19, 2017, for Application No. 2013273699, 3 pages.
(Continued)

*Primary Examiner* — Joel Lamprecht
(74) *Attorney, Agent, or Firm* — FBT Gibbons LLP

(57) ABSTRACT

A catheter is responsive to external and internal magnetic field generators for generating position data of the catheter position and pressure data to determine pressured exerted on a distal end of the catheter when engaged with tissue, with a reduced number of sensing coils and reduced number of sensing coil leads for minimizing lead breakage and failure. The catheter includes a distal section adapted for engagement with patient tissue, where the distal section has a proximal portion, a distal portion and a flexible joint with a resilient member adapted to allow axial displacement and angular deflection between the proximal and distal portions of the distal section. The catheter may have three or less sensing coils with three or less leads, each transmitting signals between a respective sensing coil and the signal processor.

20 Claims, 3 Drawing Sheets

Related U.S. Application Data continuation of application No. 16/398,059, filed on Apr. 29, 2019, now Pat. No. 11,207,000, which is a continuation of application No. 15/943,529, filed on Apr. 2, 2018, now Pat. No. 10,271,761, which is a continuation of application No. 15/351,311, filed on Nov. 14, 2016, now Pat. No. 9,931,052, which is a continuation of application No. 14/960,241, filed on Dec. 4, 2015, now Pat. No. 9,492,104, which is a continuation of application No. 13/732,316, filed on Dec. 31, 2012, now Pat. No. 9,204,820.

(51) Int. Cl.

| | |
|---|---|
| ***A61B 18/14*** | (2006.01) |
| ***A61B 34/20*** | (2016.01) |
| ***A61N 1/05*** | (2006.01) |
| *A61B 18/00* | (2006.01) |
| *A61B 90/00* | (2016.01) |

(52) U.S. Cl.
CPC ........ *A61B 5/6885* (2013.01); *A61B 18/1492* (2013.01); *A61B 34/20* (2016.02); *A61N 1/056* (2013.01); *A61B 2018/00357* (2013.01); *A61B 2018/00577* (2013.01); *A61B 2034/2051* (2016.02); *A61B 2090/065* (2016.02); *A61B 2562/0247* (2013.01)

(58) Field of Classification Search
CPC .......... A61B 34/20; A61B 2018/00357; A61B 2018/00577; A61B 2034/2051; A61B 2090/065; A61B 2562/0247; A61B 5/029; A61B 18/14; A61B 5/283; A61N 1/056
See application file for complete search history.

(56) References Cited

U.S. PATENT DOCUMENTS

| | | | | |
|---|---|---|---|---|
| 5,752,513 | A | 5/1998 | Acker et al. | |
| 6,063,022 | A | 5/2000 | Ben-Haim | |
| 6,161,032 | A | 12/2000 | Acker | |
| 6,239,724 | B1 | 5/2001 | Doron et al. | |
| 6,332,089 | B1 | 12/2001 | Acker et al. | |
| 6,427,314 | B1 | 8/2002 | Acker | |
| 6,484,118 | B1 | 11/2002 | Govari | |
| 6,574,492 | B1 | 6/2003 | Ben-Haim et al. | |
| 6,593,884 | B1 | 7/2003 | Gilboa et al. | |
| 6,600,948 | B2 | 7/2003 | Ben-Haim et al. | |
| 6,618,612 | B1 | 9/2003 | Acker et al. | |
| 6,690,963 | B2 | 2/2004 | Ben-Haim et al. | |
| 6,833,814 | B2 | 12/2004 | Gilboa et al. | |
| 6,892,091 | B1 | 5/2005 | Ben-Haim et al. | |
| 6,947,788 | B2 | 9/2005 | Gilboa et al. | |
| 7,555,330 | B2 | 6/2009 | Gilboa et al. | |
| 8,380,276 | B2 | 2/2013 | Schultz | |
| 8,437,832 | B2 | 5/2013 | Govari et al. | |
| 9,204,820 | B2 * | 12/2015 | Clark | A61B 5/6885 |
| 9,204,841 | B2 * | 12/2015 | Clark | A61B 5/065 |
| 9,492,104 | B2 * | 11/2016 | Clark | A61N 1/056 |
| 9,492,631 | B2 | 11/2016 | Tanghøj et al. | |
| 9,861,785 | B2 | 1/2018 | Clark et al. | |
| 9,931,052 | B2 * | 4/2018 | Clark | A61B 5/062 |
| 10,271,761 | B2 * | 4/2019 | Clark | A61B 5/065 |
| 11,207,000 | B2 * | 12/2021 | Clark | A61B 5/065 |
| 12,059,244 | B2 * | 8/2024 | Clark | A61B 5/062 |
| 2002/0065455 | A1 | 5/2002 | Ben-Haim et al. | |
| 2002/0165448 | A1 | 11/2002 | Ben-Haim et al. | |
| 2003/0120150 | A1 | 6/2003 | Govari | |
| 2003/0130615 | A1 | 7/2003 | Tom | |
| 2004/0068178 | A1 | 4/2004 | Govari | |
| 2007/0100332 | A1 | 5/2007 | Paul et al. | |
| 2009/0093806 | A1 | 4/2009 | Govari et al. | |
| 2009/0138007 | A1 | 5/2009 | Govari et al. | |
| 2009/0306650 | A1 | 12/2009 | Govari et al. | |
| 2010/0210938 | A1 | 8/2010 | Verard et al. | |
| 2011/0066029 | A1 | 3/2011 | Lyu et al. | |
| 2011/0196397 | A1 | 8/2011 | Frantz et al. | |
| 2012/0041295 | A1 | 2/2012 | Schultz | |
| 2012/0108988 | A1 | 5/2012 | Ludwin et al. | |
| 2014/0187917 | A1 | 7/2014 | Clark et al. | |

FOREIGN PATENT DOCUMENTS

| | | | |
|---|---|---|---|
| CN | 102423269 | A | 4/2012 |
| CN | 101416874 | B | 8/2012 |
| CN | 102727207 | A | 10/2012 |
| EP | 1184684 | A2 | 3/2002 |
| EP | 1743575 | A2 | 1/2007 |
| EP | 1878384 | A2 | 1/2008 |
| EP | 2047797 | A2 | 4/2009 |
| EP | 2130508 | A2 | 12/2009 |
| EP | 2196143 | A1 | 6/2010 |
| EP | 2279692 | A2 | 2/2011 |
| EP | 2338411 | A1 | 6/2011 |
| EP | 2462869 | A1 | 6/2012 |
| EP | 2505227 | A1 | 10/2012 |
| JP | H10-507104 | A | 7/1998 |
| JP | 2009-090114 | A | 4/2009 |
| JP | 2010-131390 | A | 6/2010 |
| JP | 2012-210410 | A | 11/2012 |
| RU | 2051614 | C1 | 1/1996 |
| WO | 1996/005768 | A1 | 2/1996 |
| WO | 2012/098551 | A1 | 7/2012 |
| WO | 2012/150567 | A1 | 11/2012 |

OTHER PUBLICATIONS

Chinese First Office Action and Search Report dated Mar. 2, 2017, for Application No. 201310752061.9, 13 pages.
European Extended Search Report and Written Opinion dated Feb. 27, 2014, for Application No. 13199537.5, 7 pages.
European Partial Search Report dated Mar. 11, 2014, for Application No. 13199522.7, 5 pages.
Japanese First Office Action dated Aug. 15, 2017, for Application No. 2013-272069, 7 pages.
Russian First Office Action dated Mar. 18, 2014, for Application No. 2013158880, 1 page.
Russian Second Office Action dated Oct. 26, 2017, for Application No. 2013158880, 6 pages.

* cited by examiner

CATHETER WITH COMBINED POSITION AND PRESSURE SENSING STRUCTURES

CROSS-REFERENCE TO RELATED APPLICATION(S)

This application is a continuation of and claims priority to and the benefit of U.S. application Ser. No. 17/561,251 filed Dec. 23, 2021, now U.S. Pat. No. 12,059,244, which is a continuation of and claims priority to and the benefit of U.S. application Ser. No. 16/398,059 filed Apr. 29, 2019, now U.S. Pat. No. 11,207,000, which is a continuation of and claims priority to and the benefit of U.S. application Ser. No. 15/943,529 filed Apr. 2, 2018, now U.S. Pat. No. 10,271,761, which is a continuation of and claims priority to and the benefit of U.S. application Ser. No. 15/351,311 filed Nov. 14, 2016, now U.S. Pat. No. 9,931,052, which is a continuation of and claims priority to and the benefit of U.S. application Ser. No. 14/960,241 filed Dec. 4, 2015, issued as U.S. Pat. No. 9,492,104, which is a continuation of U.S. application Ser. No. 13/732,316 filed Dec. 31, 2012, issued as U.S. Pat. No. 9,204,820, the entire contents of all of which are incorporated herein by reference.

FIELD OF INVENTION

The present invention relates to catheters, particular catheters with location/orientation and pressure sensing capabilities.

BACKGROUND OF INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and electrical activity in the heart chamber is detected by the electrode. Moreover, RF energy may be applied through the catheter to the electrode in order to ablate the heart tissue at the site. Proper contact between the electrode and the endocardium is necessary in order to achieve the desired diagnostic function and therapeutic effect of the catheter.

Catheters for mapping and/or ablation typically carry one or more magnetic position sensors for generating signals that are used to determine position coordinates of a distal portion of catheter. For this purpose, magnetic field generators are driven to generate magnetic fields in the vicinity of the patient. Typically, the field generators comprise coils, which are placed below the patient's torso at known positions external to the patient. These coils generate magnetic fields that are sensed by the magnetic position sensor(s) carried in the catheter. The sensor(s) generate electrical signals that are passed to a signal processor via leads that extend through the catheter.

For pressure sensing, a catheter typically carries a miniature transmitting coil and three sensing coils on opposing portions of a flexibly-jointed distal tip section. The transmitting coil is aligned with the longitudinal axis of the catheter and three sensing coils are also aligned with the longitudinal axis but positioned at an equal distance from the transmitting coil, and at equally-spaced radial positions about the longitudinal axis of the catheter. The miniature transmitting coil generates a magnetic field sensed by the three sensing coils which generate signals representative of axial displacement and angular deflection between the opposing portions of the distal tip section.

The axes of the sensing coils are parallel to the catheter axis (and thus to one another, when the joint is undeflected). Consequently, the sensing coils are configured to output strong signals in response to the field generated by the miniature field generator. The signals vary strongly with the distances of the coils. Angular deflection of the distal portion carrying the miniature field generator gives rise to a differential change in the signals output by sensing coils, depending on the direction and magnitude of deflection, since one or two of these coils move relatively closer to the field generator. Compressive displacement of the distal portion gives rise to an increase in the signals from all of three sensing coils. Prior calibration of the relation between pressure on distal portion and movement of joint may be used by processor in translating the coil signals into terms of pressure. By virtue of the combined sensing of displacement and deflection, the sensors read the pressure correctly regardless of whether the electrode engages the endocardium head-on or at an angle.

With position sensing and pressure sensing, a conventional catheter may carry six leads, one for each of the three position sensing coils and each of the three pressure sensing coil, with each lead being a twisted pair of wires. Leads are time-consuming and expensive to manufacture and install. Moreover, the leads occupy space in the space-constrained catheter tip and are susceptible to breakage. A reduction in the number of leads used in the catheter would provide a number of benefits, including reduced catheter production time, increased total catheter yield, and reduced production costs.

Accordingly, it is desirable to provide a catheter with combined or simplified position and pressure sensing capabilities for reducing the number of sensor coils and hence the number of sensor coil leads.

SUMMARY OF THE INVENTION

The present invention is directed to a catheter responsive to external and internal magnetic field generators for generating position data to determine position of the catheter within a sensing volume of magnetic fields and pressure data to determine pressured exerted on a distal end of the catheter when engaged with tissue, with a reduced number of sensing coils and hence a reduced number of sensing coil leads for minimizing lead breakage and failure.

In one embodiment, the catheter includes a distal section adapted for engagement with patient tissue, where the distal section has a proximal portion, a distal portion and a flexible joint. Either of the proximal portion or the distal portion carries an internal magnetic field generator and the other of the proximal portion or the distal portion carries a plurality of sensing coils, each mutually orthogonal to each other and sensitive both to the internal magnetic field generator for generating signals representative of pressure exerted on the distal section and to a plurality of external magnetic field generators driven by a catheterization system for generating signals representative of position of the distal section, wherein each coil has a dedicated lead adapted to transmit both the signals representative of pressure and position to a signal processor provided in the catheterization system.

In one embodiment, the flexible joint includes a resilient member adapted to allow axial displacement and angular deflection between the proximal and distal portions of the distal section.

In one embodiment, the catheter has three or less sensing coils with three or less leads, each transmitting signals between a respective sensing coil and the signal processor.

In one embodiment, the sensing coils consist of two elliptical sensors and one cylindrical (namely, longer and narrower) sensor. In a more detailed embodiment, the internal field generator is aligned with a Z axis, one elliptical sensor is aligned with an X axis, another elliptical sensor is aligned with a Y axis, and the cylindrical sensor is aligned with the Z axis.

In one embodiment, each magnetic field is distinguishable by frequency, phase and/or time.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention is directed to a system and catheter for cardiac catheterization, wherein the catheter has a sensing assembly that provides signals representative of both position of the catheter and pressure exerted on a distal section of the catheter when it engages tissue. Compared to conventional position sensing assemblies and pressure sensing assemblies, the sensing assembly of the catheter advantageously employs a reduced number of sensor coils and hence a reduced number of sensor coil leads for a simplified catheter structure that minimizes the risk of damaged or broken leads.

Figure 1:
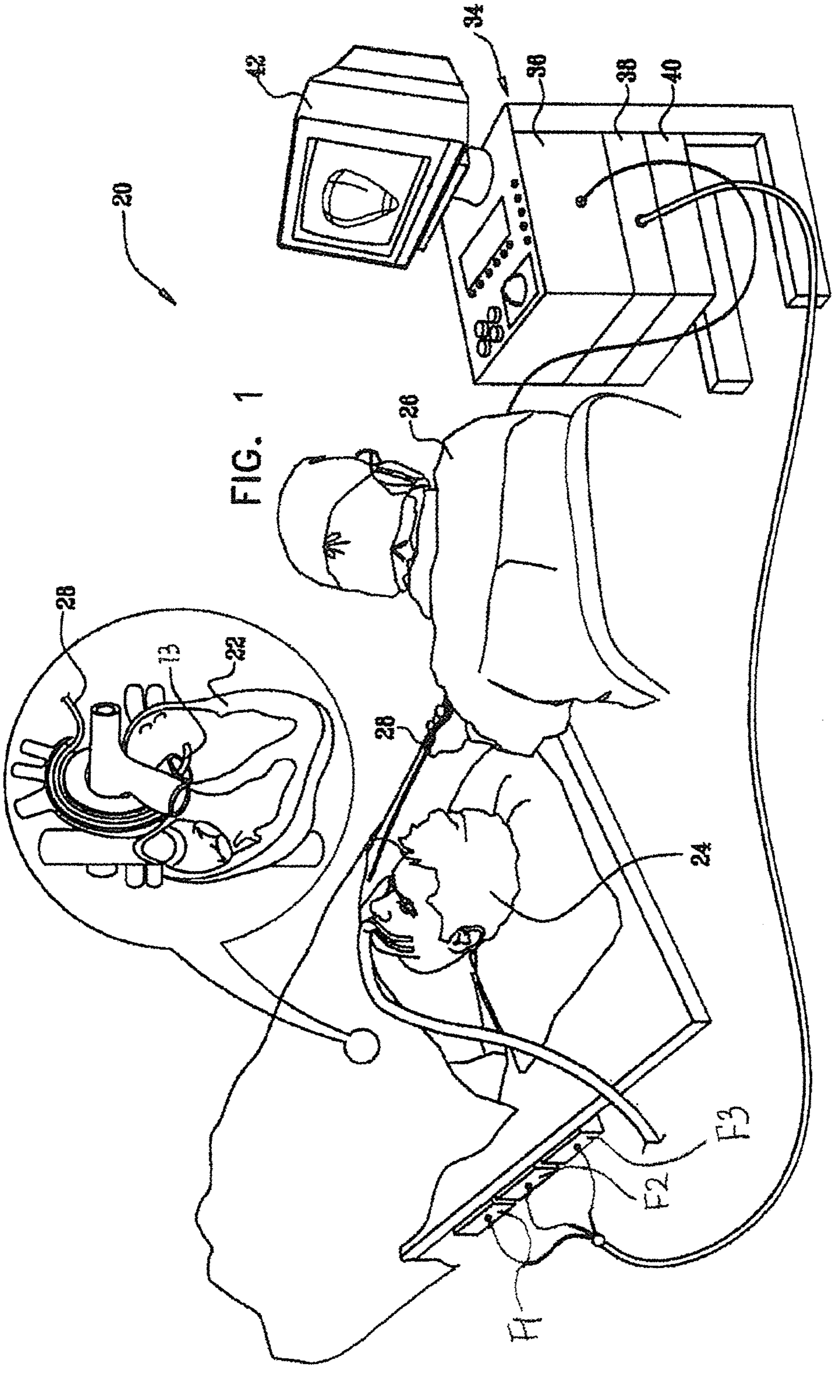
FIG. 1 is a schematic, pictorial illustration of a catheter-based medical system, in accordance with an embodiment of the present invention.
Figure 2:
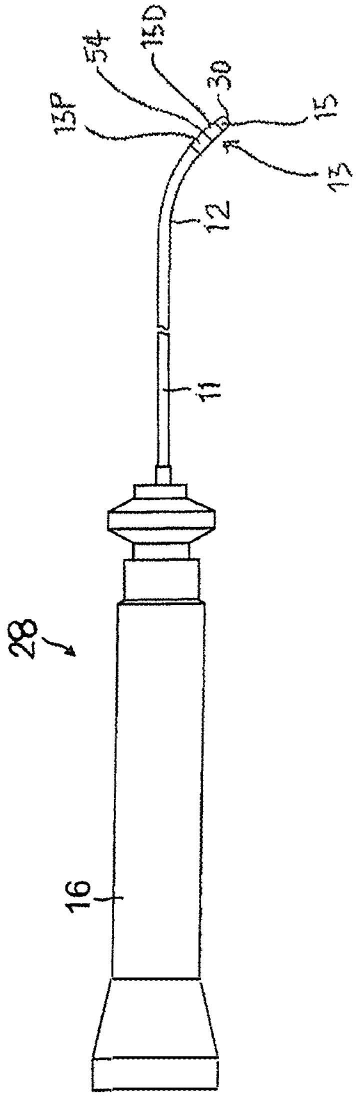
FIG. 2 is a side view of a catheter for use with the system of FIG. 1, in accordance with an embodiment of the present invention.

FIG. 1 is a schematic, pictorial illustration of a conventional system 20 for cardiac catheterization as known in the art. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used, mutatis mutandis, for other therapeutic and/or diagnostic purposes in the heart or in other body organs. As shown in FIG. 2, the catheter 28 comprises an elongated catheter body 11, a deflectable intermediate section 12, a distal section 13 carrying at least a tip electrode 15 on its distal tip end 30, and a control handle 16.

An operator 26, such as a cardiologist, inserts catheter 28 through the vascular system of a patient 24 so that a distal section 13 of the catheter enters a chamber of the patient's heart 22. The operator advances the catheter so that a distal tip 30 of the catheter engages endocardial tissue 70 at a desired location or locations. Catheter 28 is connected by a suitable connector at its proximal end to console 34. The console may comprise a radio frequency (RF) generator, which supplies high-frequency electrical energy via the catheter for ablating tissue in the heart at the locations engaged by the distal section 13. Alternatively or additionally, the catheter and system may be configured to perform other therapeutic and diagnostic procedures that are known in the art.

Console 34 uses magnetic sensing to determine data, including (i) position coordinates of the distal section 13 in the heart and (ii) its axial displacement and angular deflection due to pressure from contact with endocardial tissue 70. For the purpose of generating position data or coordinates, a driver circuit 38 in console 34 drives external magnetic field generators, for example, F1, F2 and F3, to generate magnetic fields in the vicinity of the body of patient 24 and define an external frame of reference. The generators F1, F2 and F3 are comprised of coils, which are placed below the patient's torso at known positions external to the patient. These coils generate magnetic fields within the patient's body in a predefined working volume that contains heart 22.

Figure 3:
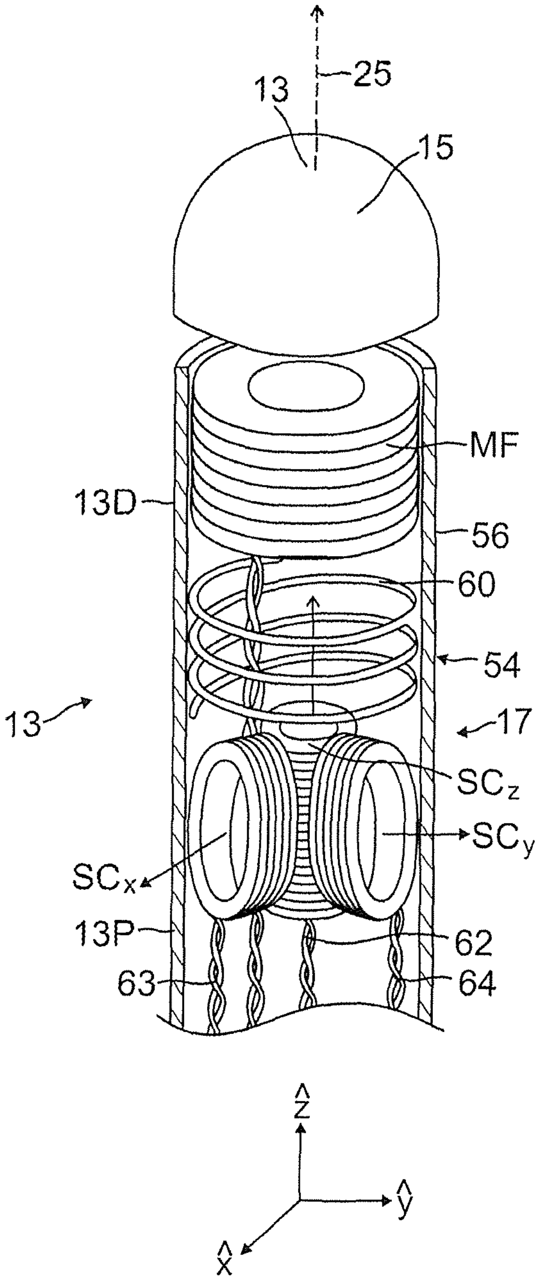
FIG. 3 is a schematic, cutaway view showing details of the distal section of the catheter of FIG. 2.

For the purpose of generating pressure data, including axial displacement and angular deflection of the distal section 13 of the catheter 28, the driver circuit 38 in console 34 drives an internal miniature magnetic field generator MF housed in a distal portion 13D of the tip section 13, as shown in FIG. 3. In the disclosed embodiment, the field generator MF comprises a coil whose axis is aligned with the Z axis defining a longitudinal axis 25 of the catheter.

With reference to FIGS. 1 and 3, a sensor assembly 17 within distal section 13 of catheter 128 is advantageously responsive to both of the field generators F1, F2, F3 and the miniature field generator MF. That is, the sensor assembly 17 generates electrical signals in response to the magnetic fields generated by the field generators F1, F2 and F3 and the miniature field generator MF.

Figure 4:
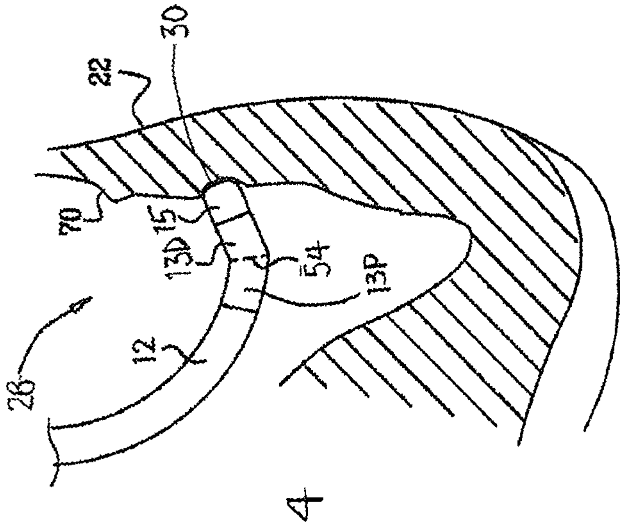
FIG. 4 is a schematic detail view showing the distal section of FIG. 3 in contact with endocardial tissue.

For detecting and measuring pressure, the distal section 13 has a proximal portion 13P and a distal portion 13D which are connected to each other by a flexible and elastic joint 54 which may be constructed of any suitable material (s) with the desired flexibility and strength. The resilient joint 54 permits a limited range of relative movement between the portions 13P and 13D in response to forces exerted on the distal section 13. Such forces are encountered when the distal tip end 30 is pressed against the endocardium during an ablation procedure. As shown in FIG. 4, the distal end 30 of catheter 28 is in contact with endocardium 70 of heart 22, in accordance with an embodiment of the present invention. Pressure exerted by the distal tip end 30 against the endocardium deforms the endocardial tissue slightly, so that the tip electrode 15 contacts the tissue over a relatively large area. Since the electrode engages the endocardium at an angle, rather than head-on, the distal portion 13D bends at joint 54 relative to the proximal portion 13P. The bend facilitates optimal contact between the electrode 15 and the endocardial tissue 70.

As shown in FIG. 3, the joint 54 comprises an outer tubing 56 which may be the outer tubing 55 of the distal section 13 which is constructed of a flexible, insulating material, such as Celcon®, Teflon®, or heat-resistant polyurethane. Or, the tubing 56 may be of a material specially adapted to permit unimpeded bending and compression of the joint. (This material is cut away in FIG. 3 in order to expose the internal structure of the catheter.) The distal section 13D is typically relatively rigid, by comparison with the remainder of the catheter.

The joint 54 further comprises a resilient coupling member 60, such as a coil spring, or a tubular piece of an elastic material with a helical cut along a portion of its length. For example, the coupling member may comprise a polymer, such as silicone, polyurethane, or other plastics, or a superelastic alloy, such as nickel titanium (Nitinol). The helical cut causes the tubular piece to behave like a spring in response to forces exerted on distal portion 13D. Further details regarding the fabrication and characteristics of this sort of coupling member are presented in U.S. patent application Ser. No. 12/134,592, filed Jun. 6, 2008, which is assigned to the assignee of the present patent application and whose disclosure is incorporated herein by reference. Alternatively, the coupling member may comprise any other suitable sort of resilient component with the desired flexibility and strength characteristics.

The stiffness of the coupling member 60 determines the range of relative movement between distal portions 13P and 13D in response to forces exerted on the distal portion 13D. Such forces are encountered when the distal tip end 30 is pressed against the endocardium during a mapping and/or ablation procedure. The desired pressure for good electrical contact between the distal portion 13D and the endocardium during ablation is on the order of 20-30 grams. The coupling member 60 is configured to permit axial displacement (i.e., lateral movement along the longitudinal axis 25 of catheter 28) and angular deflection of the distal portion 13D in proportion to the pressure on the distal tip end 30. Measurement of the displacement and deflection gives an indication of the pressure and thus helps to ensure that the correct pressure is applied during ablation.

The magnetic field sensor assembly 17 is housed in the proximal portion 113P as shown in FIG. 3. In the illustrated embodiment, the sensor 17 includes three miniature sensor coils SCx, SCy and SCz wound on air coils. The coils have generally mutually orthogonal axes, with coil SCz aligned with the longitudinal axis 25 of the catheter, which is referred to as the Z axis, the coil SCx aligned with the X axis and the coil SCy aligned with the Y axis of an (X,Y,Z) coordinate system. The three coils are all located in the same axial section at different azimuthal angles about the catheter longitudinal or Z axis, where an axial plane is defined herein as a plane perpendicular to the catheter longitudinal or Z axis and an axial section is defined herein as being contained within two axial planes of the catheter. For example, the three coils may be spaced azimuthally 120 degrees apart at the same radial distance from the axis. The three coils SCi may be a combination of position sensors and pressure sensors, such as those described in U.S. Pat. No. 6,690,963 and U.S. Publication No. 2009/0138007, the entire disclosures of which are incorporated herein by reference. In the illustrated embodiment, the sensor coil SCz is configured as a position sensor, and the sensor coils SCx and SCy are configured as pressure sensors.

Electromagnetic or magnetic fields are transmitted between the field generators F1, F2, F3 placed under the patient's torso and the sensor coils SCz, SCx and SCy housed in the catheter 28 for detecting position of the catheter. The magnetic fields created by the field generators F1, F2 and F3 cause the coils SCz, SCx and SCy to generate electrical signals, with amplitudes that are indicative of the position of the sensor assembly 17 relative to the fixed frame of reference of field generators F1, F2 and F3. In one embodiment, the three field generators F1, F2 and F3 generates a magnetic field composed of three differently-oriented field components. Each of these field components is sensed by each sensor coil SCz, SCx and SCy, each of which produces a signal composed of three components.

As shown in FIG. 1, the console 34 includes a signal processor 36 that processes these signals in order to determine the position coordinates of the distal section 13, typically including both location and orientation coordinates. This method of position sensing is implemented in the above-mentioned CARTO system and is described in detail in U.S. Pat. Nos. 5,391,199; 6,690,963; 6,484,118; 6,239,724; 6,618,612 and 6,332,089; in PCT Patent Publication WO 96/05768; and in U.S. Patent Application Publications 2002/0065455 A1, 2003/0120150 A1 and 2004/0068178 A1, all of whose disclosures are incorporated herein by reference.

For detecting and measuring pressure exerted on the distal portion 13D, an additional electromagnetic or magnetic field is transmitted by the field generator MF in the distal portion 13D and sensed by the sensor coils SCz, SCx and SCy located in the proximal portion 13D of the distal section 13. Axial displacement and/or angular deflection of the distal portion 13D relative to the proximal portion 13P gives rise to a differential change in the signal outputs by the coils SCz, SCx and SCy, depending on the direction and magnitude of deflection, since one or two of these coils move relatively closer to the field generator MF. Compressive displacement of the distal portion 13D gives rise to an increase in the signals from each of the coils SCz, SCx and SCy. Changes in the sensing of the magnetic field by generator MF causes the coils SCz, SCx and SCy to generate electrical signals, with amplitudes that are indicative of such axial displacement and/or angular deflection.

It is understood that while the coils SCx and SCy are orthogonal to and not aligned with the axis of the miniature field generator MF, the magnetic dipole field lines surrounding the field generator MF allow detection by the orthogonal coils SCx and SCy. While the coils SCx and SCy may sense a relatively weaker magnetic field by field generator MF compared to the coil SCz because of their respective orientation relative to the field generator MF, there is sufficient sensitivity for purposes of detecting and measuring pressure applied to the distal section 13. Moreover, the signal processor 36 can be calibrated to compensate for this discrepancy, as understood by one of ordinary skill in the art.

Because the coil of the generator MF in the distal portion 13D is radially symmetrical, it is well suited for on-axis alignment with the longitudinal axis 25 of the catheter. However, it is understood that the coil may also be off-axis as desired or appropriate, with the further understanding that tilting the coil off-axis will both improve certain coil(s) and degrade other coil(s) of mutually orthogonal SCx, SCy and SCz sensors.

It is also understood that the coils of the sensors SCx, SCy and SCz may be of any suitable size and shape provided they conform to packaging constraints within the distal section 13 of alignment and/or mutual orthogonality. Conventional pressure sensors tend to be cylindrical (longer and narrower) because of Z axis alignment with the generator MF within the distal section, whereas conventional X and Y position sensors tend to be more elliptical so as to maintain mutual orthogonality with the Z position sensor and conformity with the packaging constraints of the distal section. In the disclosed embodiment of the present invention, the sensor SCz configured more as a conventional pressure sensor may be more cylindrical, whereas the sensors SCx and SCy configured more as conventional position sensors may be more elliptical.

As shown in FIG. 3, lead 62 extends between the coil SCz and the signal processor 36 to pass signals from the coil SCz to the signal processor. Lead 63 extends between the coil SCx and the signal processor 36 to pass signals from the coil SCx to the signal processor. Lead 64 extends between the coil SCy and the signal processor 36 to pass signals from the coil SCy to the single processor.

Accordingly, the catheter 28 has three leads, namely, leads 62, 63 and 64 for position and pressure sensing compared to the typical five or six leads of a conventional catheter with position and pressure sensing. Each lead is time-consuming and expensive to manufacture and assemble in a catheter. Moreover, leads occupy space in a space-constrained catheter. Leads are also susceptible to breakage. Having a reduced number of sensors and hence leads, the catheter 28 provides a number of benefits, including reduced catheter production time, increased total catheter yield, and reduced production costs.

The magnetic fields generated by each field generator F1, F2, F3 and MF are distinguishable with regard to different parameters, including frequency, phase and/or time, and the signals generated by each sensor coil SCz, SCx and SCy from measuring the magnetic field flux resulting from these distinguishable magnetic fields are similarly distinguishable. Frequency, phase and/or time multiplexing is applied as appropriate or desired. For example, the current to pressure-sensing field generator MF may be generated at a selected frequency in the range between about 16 kHz and 25 kHz, while position field generators F1, F2 and F3 are driven at different frequencies.

The signal processor 36 processes these signals in order to determine data, including (i) the position coordinates of the distal section 13, typically including both location and orientation coordinates, and (ii) axial displacement and angular deflection of the distal section 13. The signal processor 36 may comprise a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as axial displacement and angular deflection of the distal tip of the catheter, and status information and guidance regarding the procedure that is in progress.

The processor 36 receives these signals via the leads 62, 63 and 64 extending through catheter 28, and processes the signals in order to derive the location and orientation coordinates of the distal section 13 in this fixed frame of reference, and to derive pressure information, including axial displacement and angular deflection of the distal section. The disposition of the coils SCz, SCx and SCy and pressure exerted on the distal portion 13D of the distal section 13 can be calculated from the characteristics of the fields, such as strength and direction, as detected by the coils. Thus, the field generators F1, F2, F3 and MF and the sensing coils SCz, SCx and SCy cooperatively define a plurality of transmitter-receiver pairs, including (F1/SCz), (F1/SCx), (F1/SCy), (F2/SCz), (F2/SCx), (F2/SCy), (F3/SCz), (F3/SCx), (F3/SCy), (MF/SCz), (MF/SCx), and (MF/SCy). Each such pair includes one field generator and a different coil as elements of the pair, with each coil disposed at a different position or orientation from the other coils. By detecting the characteristics of field transmissions between the elements of the various pairs, the system can deduce information relating to the disposition of the distal section 13 in the external frame of reference as defined by the field generators F1, F2, and F3 and information relating to pressure exerted on the distal section MF as sensed within the magnetic field generated by field generator MF. The position information can include the position of the distal section 13, the orientation of the distal section 13, or both. As understood by one of ordinary skill in the art, the calculation of position information relies upon the field generators F1, F2 and F3 being positioned in known positions and orientations relative to one another, and the calculation of pressure based on axial displacement and angular deflection relies upon the field generator MF and the sensing coils SCz, SCx and SCy being in known positions and orientations relative to each other.

The field generating coils F1, F2, F3 and MF are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

Various other configurations of the coils in the sensing assemblies may also be used, in addition to the configuration shown and described above. For example, the positions of the field generator MF and the coils SCz, SCx and SCy may be reversed, so that that field generator coil MF is in the proximal portion 13D, proximal of joint 54, and the sensor coils are in the distal portion 13D. As another alternative, coils SCz, SCx and SCy may be driven as field generators (using time- and/or frequency-multiplexing to distinguish the fields), while field generator coil MF serves as the sensor. The sizes and shapes of the transmitting and sensing coils in FIG. 3 are shown only by way of example, and larger or smaller numbers of coils may similarly be used, in various different positions, so long as one of the assemblies comprises at least two coils, in different radial positions, to allow differential measurement of joint deflection.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheterization system, comprising:

a plurality of external magnetic field generators, each generating a position-data magnetic field;

a catheter, comprising:

a flexible tubing; and a distal section adapted for engagement with patient tissue, the distal section having:

a proximal portion and a distal portion;

a distal section magnetic field generator positioned in one of the proximal and distal portions, the distal section magnetic field generator adapted to generate a pressure-data magnetic field; and first, second, and third sensors positioned in the other of the proximal and distal portions, the first sensor being configured as a position sensor, and the second and third sensors being configured as pressure sensors, the first, second, and third sensors being configured to sense each position-data magnetic field and each pressure-data magnetic field and generate signals representative of data relating to position of the distal section and data relating to pressure exerted on the distal section when engaged with the patient tissue, the first, second, and third sensors having a respective sensor lead connected thereto configured to transmit signals for signal processing; and a console configured to receive the signals from the first, second, and/or third sensor and to determine position coordinates of the distal section in response to the signals.

2. The catheterization system of claim 1, wherein the distal section further comprises a resilient coupling member between the distal portion and the proximal portion.

3. The catheterization system of claim 1, wherein the console comprises a driver circuit configured to drive the external magnetic field generators to generate magnetic fields and define an external frame of reference.

4. The catheterization system of claim 1, wherein the console is further configured to determine axial displacement or angular deflection of the distal section in response to the signals representative of data relating to pressure exerted on the distal section.

5. The catheterization system of claim 4, wherein the console comprises a driver circuit configured to drive the distal section magnetic field generator to thereby generate the signals representative of data relating to pressure exerted on the distal section, the data relating to pressure exerted on the distal section being indicative of the axial displacement or angular deflection of the distal section.

6. The catheterization system according to claim 1, wherein the signals representative of data relating to the pressure exerted on the distal section have amplitudes indicative of axial displacement or angular deflection of the distal section.

7. The catheterization system according to claim 1, wherein each of the first, second, and third sensors are generally orthogonal to an axis of the distal section magnetic field generator.

8. The catheterization system of claim 2, wherein the resilient coupling member is configured to permit axial displacement and angular deflection of the distal portion of the distal section in proportion to an amount of pressure on a distal tip end of the distal section when the distal section is engaged with the patient tissue.

9. The catheterization system of claim 1, wherein the distal section magnetic field generator is positioned in the proximal portion of the distal section, and the first, second, and third sensors are positioned in the distal portion of the distal section.

10. The catheterization system of claim 1, wherein the first, second, and third sensors are spaced azimuthally about 120 degrees apart at a same radial distance from a longitudinal axis of the catheter.

11. The catheterization system of claim 1, wherein each of the first, second, and third sensors has only one respective sensor lead.

12. The catheterization system of claim 1, wherein the catheter has first, second, and third sensor leads corresponding to the first, second, and third sensors respectively.

13. A catheterization system, comprising:

at least three external magnetic field generators, each generating a position-data magnetic field;

a catheter comprising:

an elongated catheter body; and a distal section adapted for engagement with patient tissue, the distal section having:

a proximal portion and a distal portion;

first, second, and third first coil components positioned in one of the distal portion or the proximal portion, the first, second, and third first coil components each configured to generate a pressure-data magnetic field or a position-data magnetic field;

a second coil component positioned in the other of the distal portion or the proximal portion, the second coil component configured to sense each position-data magnetic field and each pressure-data magnetic field and generate signals representative of data relating to position of the distal section and data relating to pressure exerted on the distal section when engaged with the patient tissue; and a console configured to receive the signals from the second coil component and to determine position coordinates of the distal section in response to the signals.

14. The catheterization system of claim 13, wherein the pressure-data magnetic fields or position-data magnetic fields generated by the first, second, and third first coil components are distinguishable by time-multiplexing and/or frequency-multiplexing.

15. The catheterization system according to claim 13, wherein the second coil component is positioned in the proximal portion of the distal section, and the first, second, or third first coil components are positioned in the distal portion of the distal section.

16. The catheter of claim 13, wherein the distal section further comprises a resilient coupling member between the distal portion and the proximal portion.

17. The catheterization system of claim 13, wherein the first, second, and third first coil components are spaced azimuthally about 120 degrees apart at a same radial distance from a longitudinal axis of the catheter.

18. The catheterization system of claim 13, wherein the console is further configured to determine axial displacement or angular deflection of the distal section in response to the signals representative of data relating to pressure exerted on the distal section.

19. The catheterization system of claim 18, wherein the console comprises a driver circuit configured to drive the first, second, and third first coil components to thereby generate the signals representative of data relating to pressure exerted on the distal section, the data relating to pressure exerted on the distal section being indicative of the axial displacement or angular deflection of the distal section.

20. The catheterization system of claim 13, wherein the catheter has first, second, and third sensor leads corresponding to the first, second, and third first coil components respectively.

* * * * *